(12) United States Patent
Yoneda (10) Patent No.: US 7,806,540 B2
(45) Date of Patent: Oct. 5, 2010

(54) ILLUMINATION DEVICE

(75) Inventor: Kenji Yoneda, Kyoto (JP)

(73) Assignee: CCS, Inc., Kyoto (JP)

( * ) Notice: Subject to any disclaimer, the term of this patent is extended or adjusted under 35 U.S.C. 154(b) by 53 days.

(21) Appl. No.: 12/064,696

(22) PCT Filed: Aug. 24, 2006

(86) PCT No.: PCT/JP2006/316602

§ 371 (c)(1),
(2), (4) Date: Feb. 25, 2008

(87) PCT Pub. No.: WO2007/023891

PCT Pub. Date: Mar. 1, 2007

(65) Prior Publication Data

US 2009/0129121 A1 May 21, 2009

(30) Foreign Application Priority Data

Aug. 26, 2005 (JP) ............................ P2005-245204

(51) Int. Cl.
*F21V 8/00* (2006.01)
*F21V 13/04* (2006.01)
(52) U.S. Cl. ............... 362/27; 362/612; 362/249.02; 362/249.06
(58) Field of Classification Search ............ 362/27, 362/29, 30, 612, 555, 216, 249.02, 249.06
See application file for complete search history.

(56) References Cited

U.S. PATENT DOCUMENTS

| | | | | |
|---|---|---|---|---|
| 5,899,557 A | * | 5/1999 | McDermott | 362/244 |
| 5,949,346 A | * | 9/1999 | Suzuki et al. | 340/815.45 |
| 6,053,621 A | * | 4/2000 | Yoneda | 362/245 |
| 6,647,199 B1 | | 11/2003 | Pelka et al. | |
| 6,900,059 B1 | * | 5/2005 | Shinn et al. | 436/43 |
| 7,128,460 B2 | * | 10/2006 | Hosobuchi | 362/626 |

FOREIGN PATENT DOCUMENTS

| | | |
|---|---|---|
| EP | 0 732 679 | 9/1996 |
| JP | 04-138612 | 5/1992 |
| JP | 5-63050 | 8/1993 |
| JP | 10-021717 | 1/1998 |

* cited by examiner

*Primary Examiner*—Stephen F. Husar
*Assistant Examiner*—Peggy A. Neils (57) ABSTRACT

A lighting device is provided that surface-emits the light evenly with less number of luminous bodies by comprising a transparent body 2 for light diffusion in a shape of a body of rotation having a center bore 11 and provided with a luminous surface 2c and a light introducing surface 2b, and multiple luminous bodies 3 that introduce the light into the light introducing surface 2c of the transparent body 2 and make the luminous surface 2c of the transparent body 2 surface-emit the light, wherein the light introducing surface 2b is arranged on an inner peripheral section forming the center bore 11 of the transparent body 2, a reflecting layer 41 is arranged to reflect the light on a surface other than the light introducing surface 2b and the luminous surface 2c of the transparent body 2, and the light from the luminous bodies 3 is emitted toward an outer surrounding surface 2e of the transparent body 2.

7 Claims, 8 Drawing Sheets

Fig.8

ILLUMINATION DEVICE

FIELD OF THE ART

This invention relates to a lighting device that surface-emits the light and that is preferably used in case of inspecting a product by making use of backlight lighting.

BACKGROUND ART

As a method for inspecting a surface of a product, generally known conventional method is a method wherein the light is irradiated on the product from upward by the use of a lighting device having a luminous section on its lower surface and inspection is conducted by means of monitoring or filming the reflecting light at a position near the lighting device. At this time, if the luminous intensity on the surface to be inspected is uneven, there might be a case of failing in detecting a minute flaw on a surface to be inspected or a defect of finishing. As a result, multiple luminous bodies such as multiple LEDs are used as the luminous section wherein the multiple luminous bodies are arranged on the under surface of the lighting device thoroughly, the luminous bodies emit light downward and the luminous intensity on the surface to be inspected is kept even and constant.

However, with the lighting device of the above-mentioned arrangement, since the luminous bodies are arranged on the under surface of the lighting device thoroughly, a large number of the luminous bodies is required, thereby taking considerable time for assembling. In addition, since the luminous intensity on the surface to be inspected becomes uneven to some extent and the unevenness of the luminous intensity on the surface to be inspected might be further promoted due to fluctuation of the direction in which each luminous body is mounted when assembling the lighting device, precise assembly accuracy is also required. Furthermore, in case that the surface to be inspected is a gloss surface, the luminous body itself is reflected on the gloss surface, thereby failing in detecting the surface state of the specimen.

As a result, in order to solve the problems of the above-mentioned conventional lighting device, the present claimed inventor has developed a lighting device (patent document 1) wherein multiple luminous bodies are arranged on an outer surrounding surface of a plate-shaped transparent body having a center bore and light is emitted toward the center bore from the luminous bodies arranged on the outer surrounding surface so that a lower surface of the transparent body surface-emits the light. With this lighting device (hereinafter called as a prior lighting device), an effect can be produced that the luminous surface emits the light with an even luminous intensity. As a result of this, the luminous intensity on the surface to be inspected also becomes even and constant so as to preferably detect a defect such as a microscopic flaw or a defect of finishing on the surface to be inspected.

Patent document 1: Japan Patent Laid-open number 10-21717

DISCLOSURE OF THE INVENTION

Problems to be Solved by the Invention

However, there is a case that an area on which light is irradiated may be smaller than that of the prior lighting device depending on a shape of the object to be inspected or a portion to be inspected. In this case, there is a need for a lighting device that can produce the same effect as that of the prior lighting device with less number of luminous bodies and at a lower cost. More specifically, it is enough for a backlighting used at a time of inspecting a notch for positioning of a silicon wafer to irradiate the light on only a surrounding section of the silicon wafer and there is no need of irradiating the light on a whole area of the silicon wafer.

With the view of the above problems, a main object of the present claimed invention is to provide a compact and low-cost lighting device that surface-emits the light evenly with less number of luminous bodies.

Means to Solve the Problems

More specifically, the lighting device in accordance with this invention comprises a transparent body for light diffusion in a shape of a body of rotation having a center bore and provided with a luminous surface and a light introducing surface, and multiple luminous bodies that introduce the light into the light introducing surface of the transparent body and make the luminous surface of the transparent body surface-emit the light, and is characterized by that the light introducing surface is arranged on an inner peripheral section forming the center bore of the transparent body, a reflecting layer is arranged to reflect the light on a surface other than the light introducing surface and the luminous surface of the transparent body, and the light from the luminous bodies is emitted toward an outer surrounding surface of the transparent body.

In case of making a predetermined surface surface-emit the light by introducing the light from the light source into the transparent body where the reflecting layer is arranged, since the light emitted from the luminous bodies as being the light source is regular-reflected or scatter-reflected on the reflection surface of the transparent body and introduced into the luminous surface while being stirred, unevenness of the light density is eliminated and the light emitted from the luminous bodies is led out through the luminous surface without loss. The shorter a distance from the light source to the luminous surface is, the less sufficient the light is stirred by the reflecting surface. If the distance from the light source to the luminous surface is short, the luminous intensity on the luminous surface becomes uneven because the directional characteristic of the light just after irradiation from the light source is reflected. Meanwhile, if the distance from the light source to the luminous surface is long, the light is fully stirred on the reflecting layer. As a result, unevenness of the luminous intensity on the luminous surface becomes less. For this reason, in case that the light is surface-emitted from the surrounding edge section of the transparent body in a shape of a body of rotation of the same size having a center bore by the luminous bodies whose number is the same, the lighting device in accordance with the present claimed invention wherein the light is introduced from inside toward outside can reduce unevenness of the luminous intensity on the luminous surface and the luminous surface can emit light evenly compared with a prior lighting device wherein the luminous bodies are arranged on the outer surrounding surface of the transparent body. Meanwhile, in order to make the distance from the light source to the luminous surface equal, it is necessary for the lighting device wherein the luminous bodies are arranged on the outer surrounding section of the transparent body to enlarge a radius of the body of rotation compared with the lighting device wherein the luminous bodies are arranged on the inner peripheral section of the transparent body.

In addition, in case of making an edge section of the transparent body whose shape is a body of rotation having a center bore surface-emit the light by the same number of the luminous bodies as the light source, the difference in the light density becomes big because each interval between the luminous bodies of the lighting device wherein the luminous bodies are arranged on the outer surrounding section of the transparent body becomes wider than that of the lighting device wherein the luminous bodies are arranged on the inner peripheral section of the transparent body. This also becomes a cause of the unevenness of the luminous intensity on the luminous surface.

As a result, with the lighting device in accordance with this invention, in case that the luminous surface is arranged on the surrounding section of the transparent body, since the distance between the luminous bodies can be secured and the light can be fully stirred on the reflecting layer even though the size of the transparent body is small and almost the same as that of an object to be irradiated, it is possible to surface-emit the light evenly with a downsized structure, less number of luminous bodies and at a lower cost.

In addition, among the reflecting layers arranged on the surface other than the light introducing surface and the luminous surface if the reflecting layer arranged on a surface facing the luminous surface of the transparent body scatter-reflects the light, the light emitted from the luminous bodies is fully scattered and stirred in the transparent body prior to leading out from the luminous surface, then the luminous surface emits the light with more even luminous intensity.

Furthermore, if a space between the luminous body and the transparent body is filled with transparent resin such as silicone resin having a refractive index approximate to that of the transparent body, the light emitted from the luminous bodies is introduced into the transparent body without loss, thereby enabling the luminous surface to surface-emit the light effectively with less number of the luminous bodies.

A shape of the transparent body used for the lighting device in accordance with this invention is not particularly limited as far as a body of rotation having a center bore, however, if the transparent body is in a shape of a disk and the luminous surface is set on a surface perpendicular to the center axis, it is possible to obtain an excellent surface light source wherein the light travels toward the specimen from one direction. In addition, in case that the luminous surface of the transparent body is in a shape of a concave surface of a circular cone with its head cut, since the luminous surface is tilted to lower from the surrounding edge section toward the center bore, if a specimen to be backlighted is wet and droplet is dropped on the luminous surface from the specimen, the droplet can be discharged through the center bore.

The lighting device having the above arrangement can be used for the lighting device for backlight, and can be preferably used for inspection of, for example, a notch for positioning of a silicon wafer. In case of using the lighting device in accordance with this invention as the backlight lighting device, it is preferable that the luminous bodies are LEDs that emit the red light or the infrared light.

As another embodiment of the lighting device in accordance with this invention represented is a lighting device comprising a transparent body for light diffusion having a center bore and provided with a luminous surface and a light introducing surface, and multiple luminous bodies that introduce the light into the light introducing surface of the transparent body and make the luminous surface of the transparent body surface-emit the light, wherein the light introducing surface is arranged on an inner peripheral section forming the center bore of the transparent body, a reflecting layer is arranged to reflect the light on a surface other than the light introducing surface and the luminous surface of the transparent body, and the light from the luminous bodies is emitted toward an outer surrounding surface of the transparent body.

EFFECT OF THE INVENTION

In accordance with this invention, since it is possible to provide an inexpensive and compact lighting device having the luminous surface that surface-emits the light having even luminous intensity with less number of the luminous bodies, if the lighting device is used as the backlight lighting device, it is possible to detect a minute flaw that might be generated on an inspected area or a defect of finishing with an attempt to reduce its cost.

BRIEF DESCRIPTION OF THE DRAWINGS

FIG. 7 is a front view (a) and a partially cross-sectional view (b) of the luminous body mounting substrate in accordance with further different embodiment of the present claimed invention.

EXPLANATION OF THE CODES

2 . . . transparent body
2c . . . luminous surface
2b . . . light introducing surface
2e . . . outer surrounding surface
3 . . . luminous body
11 . . . center bore

BEST MODES OF EMBODYING THE INVENTION

One embodiment of the present claimed invention will be explained with reference to drawings.

Figure 1:
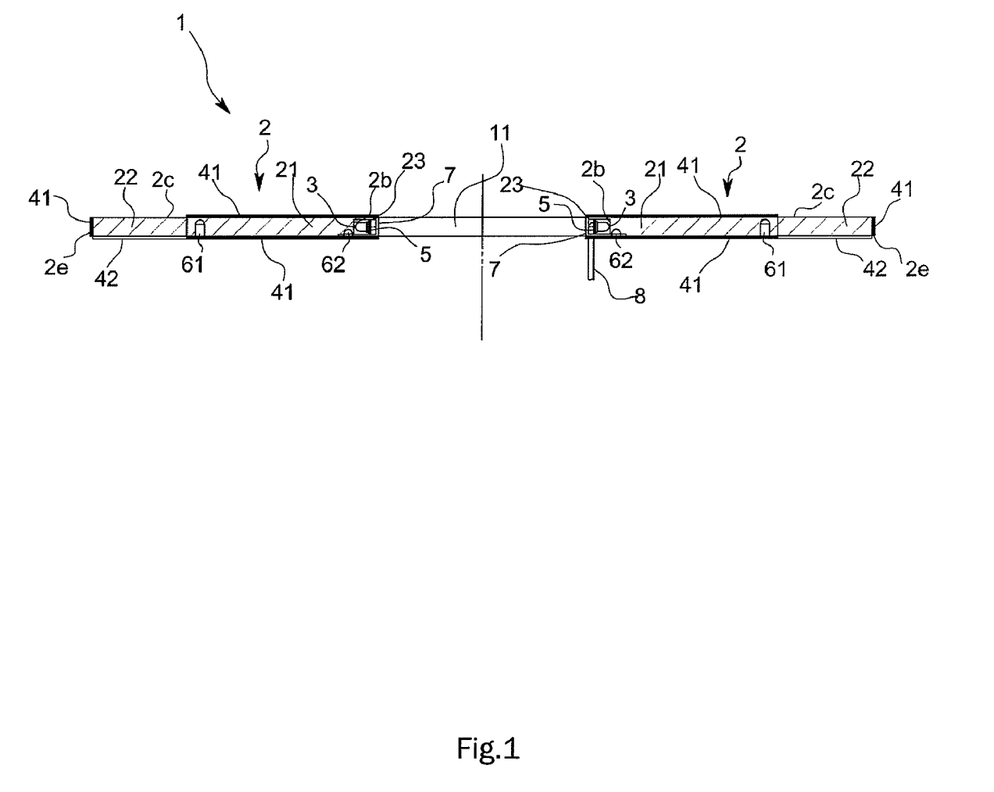
FIG. 1 is a transverse sectional view showing the lighting device in accordance with one embodiment of the present claimed invention.
Figure 2:
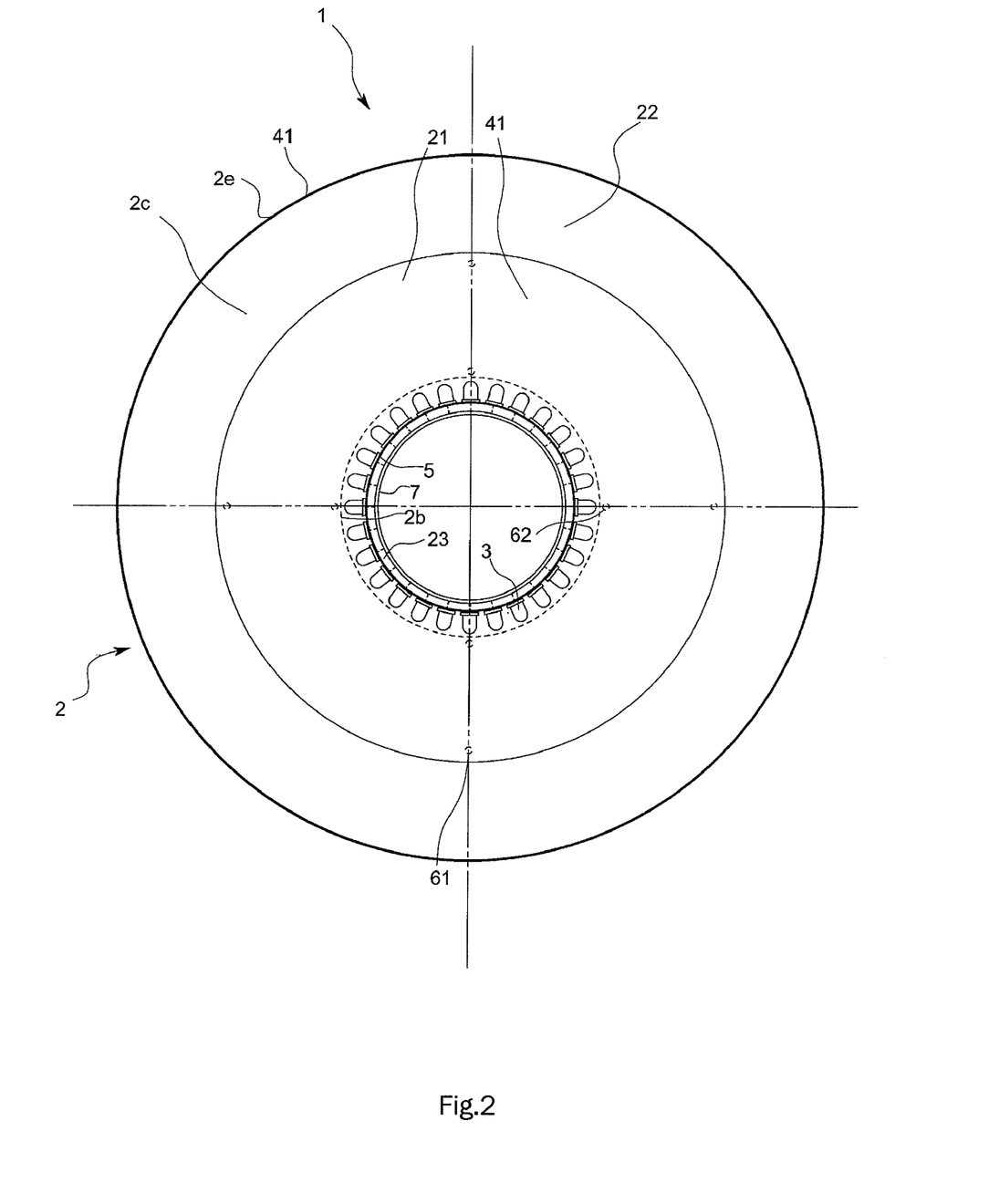
FIG. 2 is a top view of the lighting device in accordance with this embodiment.

A lighting device 1 in accordance with this embodiment comprises, as shown in FIG. 1 and FIG. 2, a transparent body 2 in a shape of a disk having a center bore 11 and multiple luminous bodies 3 such as LEDs arranged to face an inner peripheral section, more specifically, an inner peripheral surface 2b that is parallel to the center axis of the transparent body 2 and whose light is introduced in a direction orthogonal to the center of axle of the center bore 11 toward an outer surrounding surface 2e of the transparent body 2. The inner peripheral surface 2b of the transparent body 2 becomes the light introducing surface 2b that introduces the light emitted from the luminous bodies 3 into the transparent body 2 and an upper surface of the transparent body 2 becomes a luminous surface 2c with an annular ring shape that leads the light emitted from the luminous bodies 3 outside of the transparent body 2.

In this embodiment, the transparent body 2 comprises a light introducing section 21 arranged in a certain area of an inner peripheral side of the transparent body 2, a luminous section 22 arranged in an outer surrounding side of the light introducing section 21 and a flange 23 arranged to protrude on a surface extending from the luminous surface 2c so as to be orthogonal to the light introducing surface 2b from the light introducing surface 2b toward the center bore 11. A reflecting layer 41 that is made of a mirror or a transparent body and that regular-reflects the light is arranged on an upper surface and a lower surface of the light introducing section 21 and the outer surrounding surface 2e, and a reflecting layer 42 that is coated in white and that scatter-reflects the light is arranged on a lower surface of the luminous section 22, more specifically, a surface facing the luminous surface 2c. In addition, microscopical concavity and convexity are arranged on the luminous surface 2c of the transparent body 2 so that the luminous surface 2c is in a state of a frosted glass surface. An internally threaded bore 61 on the lower surface of the light introducing section 21 is to mount the lighting device 1 of this embodiment.

The luminous bodies 3 are loaded on a flexible luminous body mounting substrate 5 such as a flexible substrate and arranged to face the light introducing surface 2b of the transparent body 2, and transparent resin such as silicone resin whose refraction index is close to that of the transparent body 2 is filled in a space between the luminous body 3 and the transparent body 2. Electric power is supplied to each luminous body 3 from an electric supply cable 8 through the luminous body mounting substrate 5.

The inner peripheral section of the transparent body 2 comprising the light introducing surface 2b and the flange 23 that is orthogonal to the light introducing surface 2b of the transparent body 2 is blocked off by a cover section 7 with accommodating the luminous bodies 3. The cover section 7 is fixed to the inner peripheral section of the transparent body 2 by means of a screw hole 62.

Figure 3:
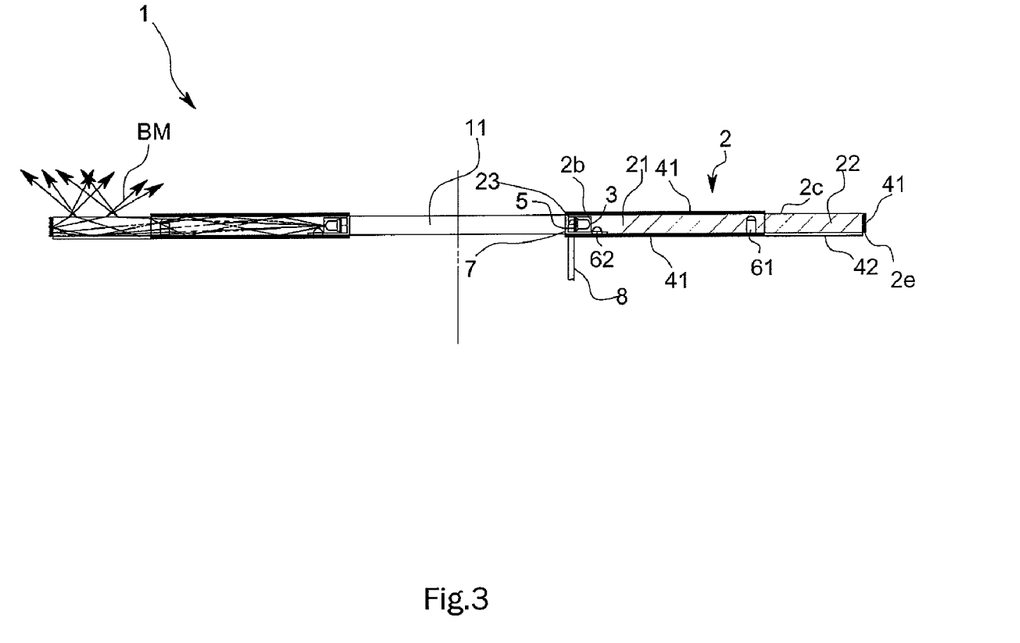
FIG. 3 is a transverse sectional view of the lighting device showing a general traveling path of the light when the lighting device is turned on in accordance with this embodiment.

In accordance with this arrangement, a case when the lighting device 1 of this embodiment is lit will be explained with reference to FIG. 3. The light emitted by each luminous body 3 travels inside the transparent resin without almost any loss and is introduced into inside of the transparent body 2 through the light introducing surface 2b and then diffuses in the direction of right, left, up or down. Then as shown by the light beam BM in FIG. 3, the light emitted from the luminous bodies 3 is regular-reflected on the reflecting layer 41 arranged on the upper and lower surfaces of the light introducing section 21 and the outer surrounding surface 2e of the transparent body 2, travels inside the transparent body 2 until it reaches near the luminous surface 2c, and is further scatter-reflected on the reflecting layer 42 arranged to face the luminous surface 2c of the luminous section 22 of the transparent body 2, a part of the light is scattered also on the luminous surface 2c of the transparent body 2, and is finally emitted from the luminous surface 2c of the transparent body 2 uniformly. When the light is emitted from the luminous surface 2c, since the luminous surface 2c is in a state of the frosted glass, the light is further scattered. As a result, whole of the luminous surface 2c surface-emits the light with a uniform luminous intensity.

In accordance with this arrangement, since the light emitted from the luminous bodies 3 is regular-reflected and stirred on the reflecting layer 41 arranged on the upper and lower surfaces of the light introducing section 21 and the outer surrounding surface 2e of the transparent body 2 and introduced inside the transparent body 2 without loss until it reaches the luminous surface 2c, it is possible to maintain the luminous intensity of the luminous surface 2c even though a total number of the luminous bodies is reduced. In addition, since the light travels while being regular-reflected on the reflecting layer 41 and scatter-reflected on the reflecting layer 42 even though a direction to which each luminous body 3 faces deviates to some extent, it is unlikely to generate unevenness in the luminous intensity. In addition, since a thickness of the lighting device 1 can be set to be almost the same as an outer size of the luminous body 3, the lighting device 1 can be made low-bulky and eventually downsized.

Figure 4:
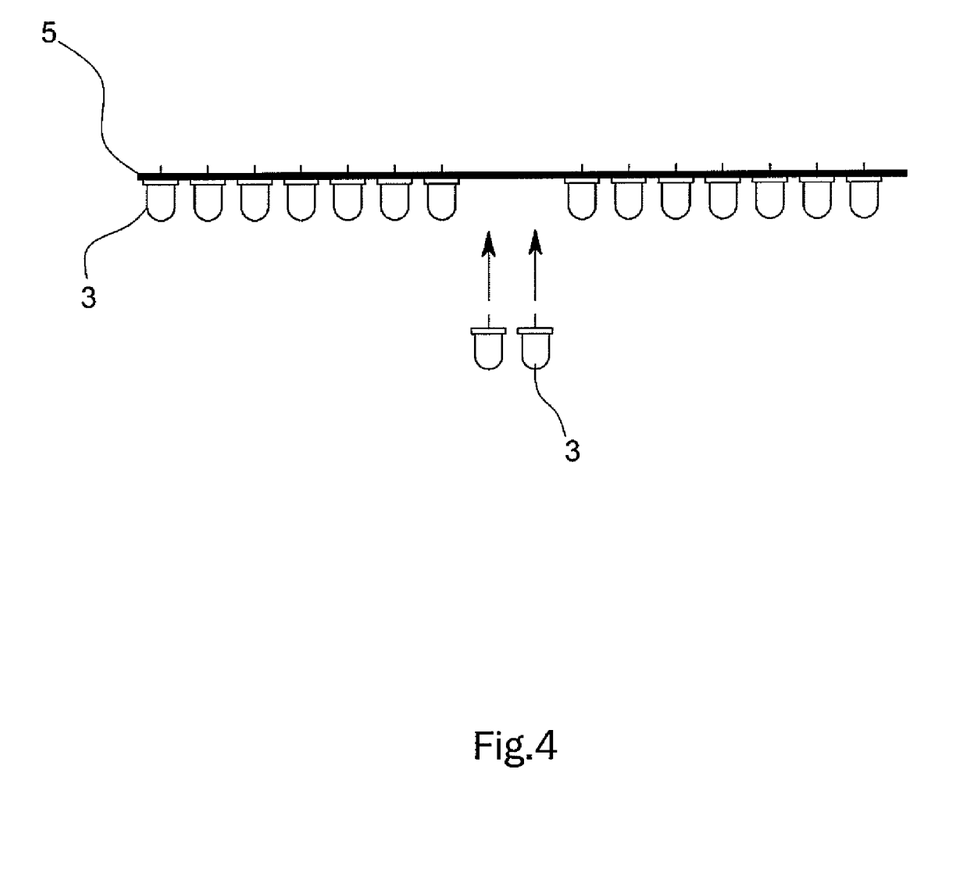
FIG. 4 is a front view showing the luminous body mounting substrate on which the luminous bodies are loaded prior to assembling the lighting device in accordance with this embodiment.
Figure 5:
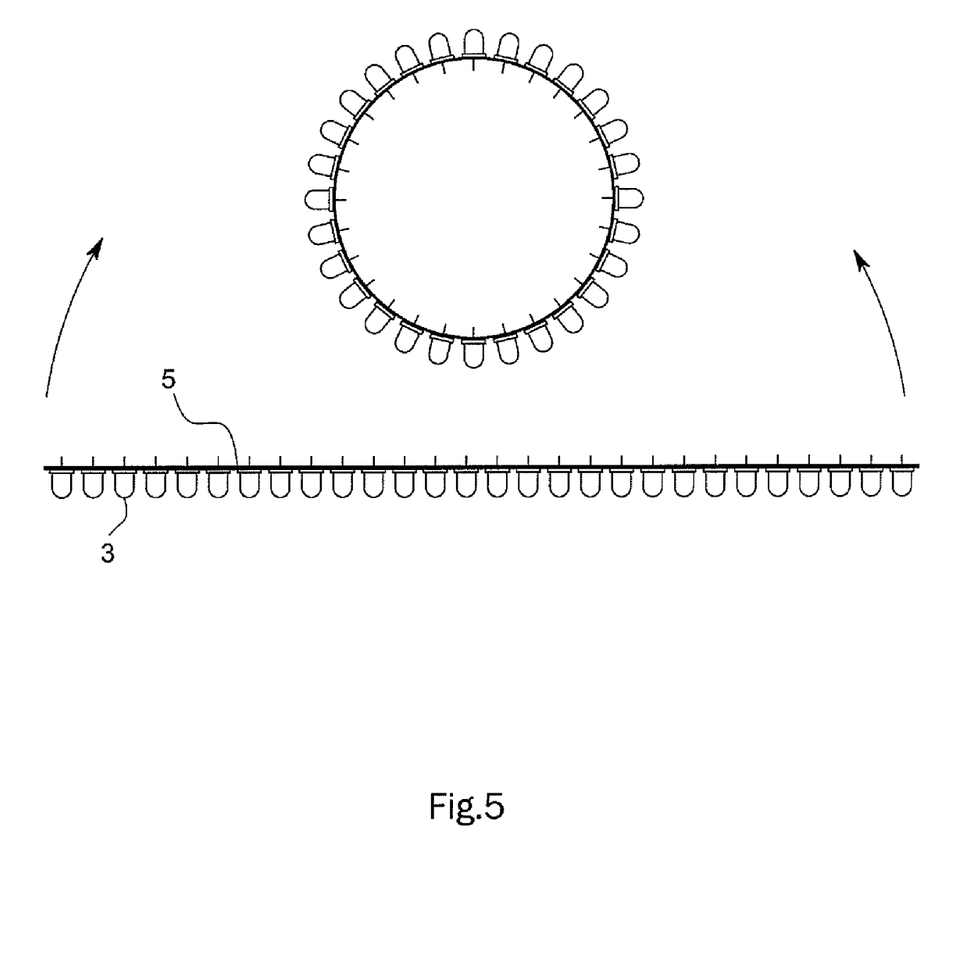
FIG. 5 is a front view showing the luminous body mounting substrate in accordance with this embodiment in case of mounting the luminous body mounting substrate on the inner peripheral section of the transparent body by bending the luminous body mounting substrate to be in a circle shape.

Next, a method for assembling the lighting device 1 in accordance with this embodiment will be explained with reference to FIG. 4 and FIG. 5, especially, with a focus on mounting the luminous bodies 3. The transparent body 2 is assembled with the following procedures; first the luminous body mounting substrate 5 is arranged linearly as shown in FIG. 4, each luminous body 3 is mounted on the luminous body mounting substrate 5 in line, next the luminous body mounting substrate 5 loaded with the luminous bodies 3 is placed on the flange 23 so that the luminous bodies 3 locate outside and face the light introducing surface 2b of the transparent body 2 by making use of a characteristic that the luminous body mounting substrate 5 is made of a flexible material such as a flexible substrate, and transparent silicon is filled into a space between the luminous bodies 3 and the transparent body 2, finally the cover section 7 is mounted. The reflecting layers 41, 42 may be previously arranged or may be arranged after the luminous bodies 3 are mounted. In addition, the electric power cable 8 is loaded on the luminous body mounting substrate 5 at the same time when the luminous bodies 3 are loaded at a time shown in FIG. 4. As mentioned, the lighting device 1 in accordance with this invention is completed. As a result, it becomes possible to load the luminous bodies 3 on the luminous body mounting substrate 5 in a manner the same as that of a conventional manner wherein electronic components are loaded on an ordinary substrate. In addition, since a total number of the luminous bodies 3 is low as mentioned above and restrictions of assembling the lighting device 1 is reduced because the fluctuation affects the performance of the lighting device 1 is small even though each luminous body 3 is loaded in a direction with some fluctuation, time required for assembling becomes short and assembling procedure becomes simple as well.

The present claimed invention is not limited to the above-mentioned embodiment.

Figure 6:
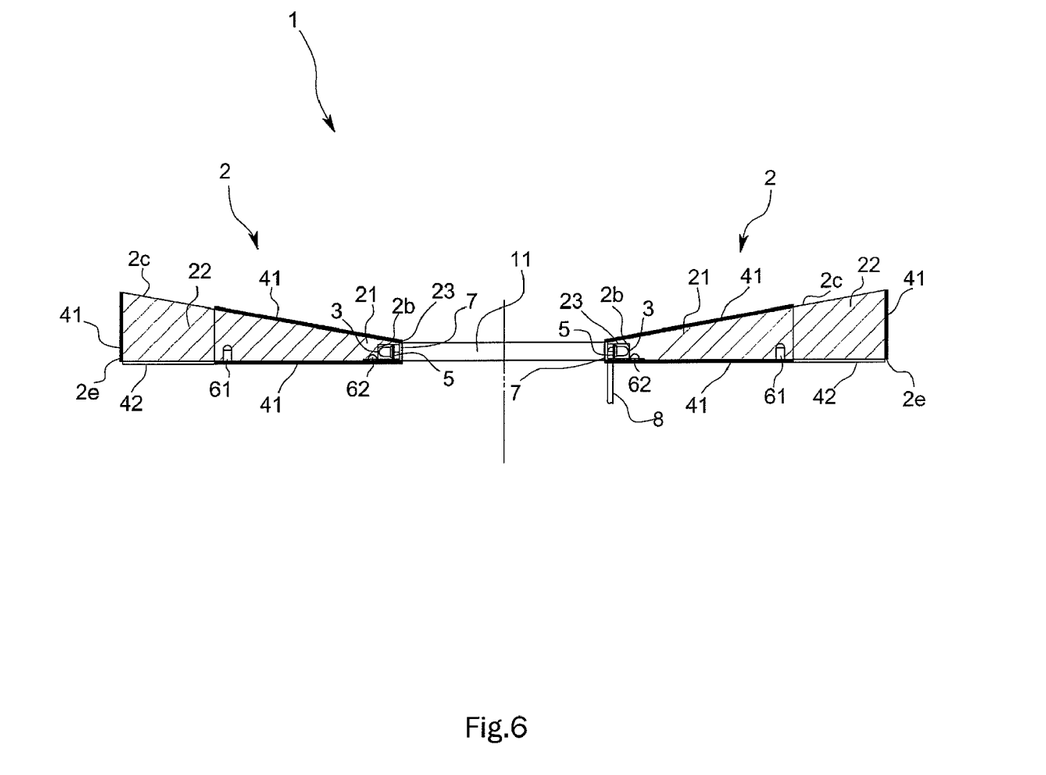
FIG. 6 is a transverse sectional view of the lighting device in accordance with another embodiment of the present claimed invention.

For example, the luminous surface 2c may be in a shape of a concave of a circular cone with its head cut as shown in FIG. 6. In accordance with this arrangement, in case that the lighting device 1 in accordance with this invention is used as a backlight lighting device and its specimen is wet, droplet that drops on a luminous surface 2c from the specimen slips off toward the center bore 11 and is discharged from the center bore 11 with ease.

Figure 7:
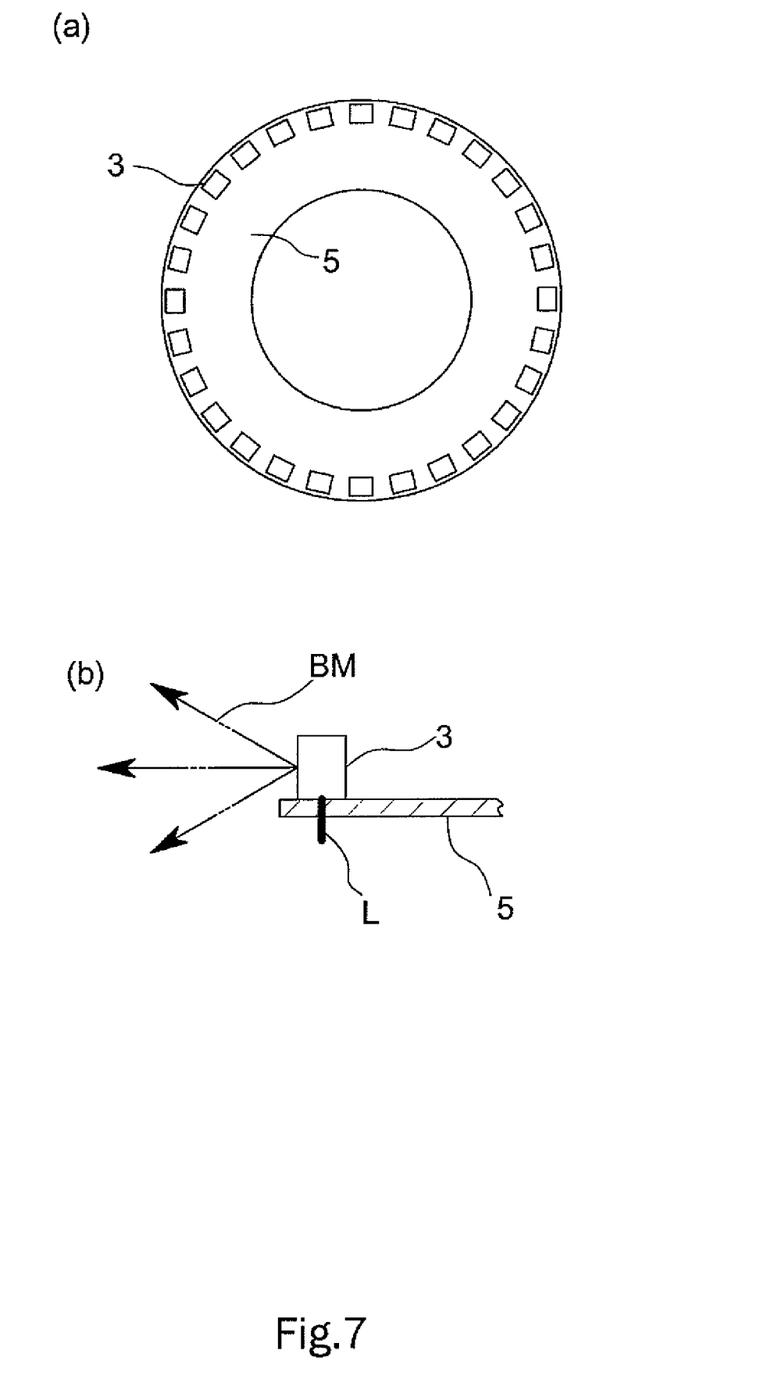

In addition, as shown in FIG. 7, a side view style of a luminous body may be used as the luminous body 3 and the luminous body mounting substrate 5 may be disk-shaped. In this case, it is possible to mount the luminous bodies 3 on the substrate 5 of a disk shape having a center bore in a standing posture along an outer circumference of the substrate 5 so that a luminous surface of the luminous body 3 faces a direction of the outer circumference by fittingly inserting a lead L of the luminous body 3 into a through hole (not shown in drawings) arranged on the substrate 5. In this case, the lighting device 1 is assembled by fittingly inserting the substrate 5 on which the luminous bodies 3 are mounted into the center bore 11 of the transparent body 2.

Furthermore, the transparent body 2 may be colored in an arbitrary color. The luminous bodies 3 may be stroboscopically illuminated and may be set circumferentially in multiple lines if a bigger luminous intensity is required. The luminous body 3 is not limited to a monochromatic light, and red, blue and green may be used by mixture and the luminous surface 2c may emit the light in an arbitrary color by making use of its mixing ratio.

The space between the transparent body 2 and the luminous body 3 may not be filled with the transparent resin. In this case, some uneven light emission might be generated near the light introducing surface 2b of the transparent body 2, however, enough lighting performance can be produced depending on an object to be inspected.

Multiple concave sections may be arranged on the inner peripheral section of the transparent body 2 and the luminous body 3 may be accommodated in each of the concave sections.

A ratio of the light introducing section 21 and the luminous section 22 of the transparent body 2 can be varied arbitrarily according to an object to be illuminated and the luminous section 22, namely the luminous surface 2c may be further narrowed.

Figure 8:
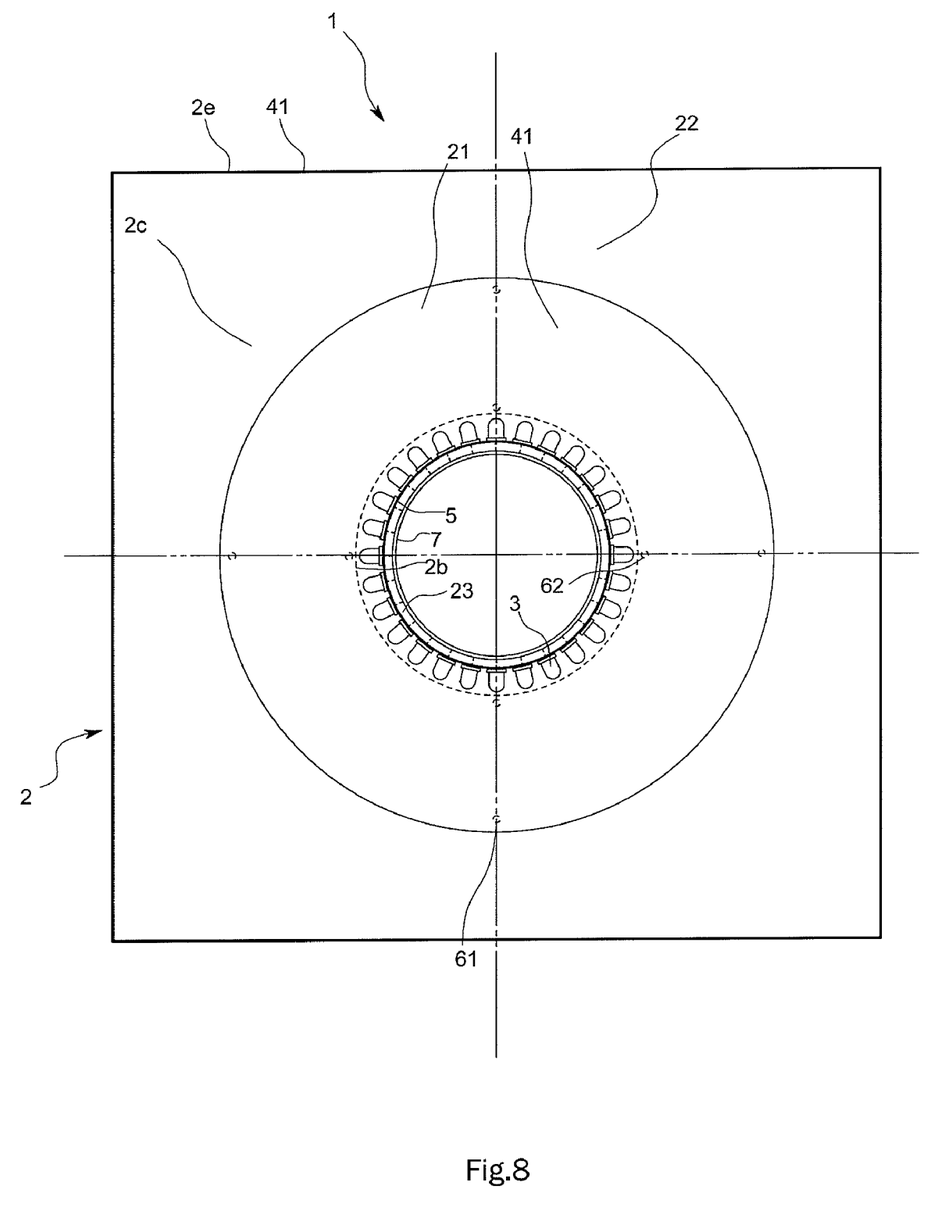
FIG. 8 is a top view of the lighting device in accordance with further different embodiment of the present claimed invention.

In addition, a shape of the transparent body used for the lighting device in accordance with this invention is not especially limited to a body of rotation having a center bore, and may be, for example, rectangle as shown in FIG. 8.

Furthermore, a shape of the center bore for monitoring or filming the specimen such as a product is circle in plane view, however, it is not limited to this and may be, for example, rectangle in plane view.

The present claimed invention is not limited to above-mentioned each embodiment, and a part or all of the above-mentioned various configurations may be appropriately combined without departing from the spirit of the invention.

POSSIBLE APPLICATIONS IN INDUSTRY

The lighting device having the above arrangement in accordance with the present claimed invention can be used as a backlight lighting device and preferably used, for example, in case of inspecting a notch for positioning of a silicon wafer.

The invention claimed is:

1. A lighting device for examining quality of a product, comprising:
    a transparent disk with a cylindrical bore on a central axis and a cylindrical outer wall, the cylindrical bore having a light introducing surface on an inner periphery of the cylindrical bore;
    a plurality of spaced luminous bodies are mounted on a flexible luminous body mounting substrate of an elongated configuration, the luminous body mounting substrate is mounted adjacent the light introducing surface to enable the spaced luminous bodies to direct light radially outward within the transparent disk; and
    a reflective member is provided on the cylindrical outer wall, an upper surface of the transparent disk and a lower surface of the transparent disk except for an annular ring of a light emitting luminous surface on the transparent disk which is spaced radially outward from the cylindrical bore to enable light emissions parallel to the central axis, wherein the light emitting luminous surface has a light scattering property to emit a uniform luminous intensity of light to the product.

2. A backlight lighting device using the lighting device described in claim 1.

3. The lighting device of claim 1 wherein a space between the luminous bodies and the transparent disk is filled with a transparent resin of a matching index of refraction.

4. The lighting device of claim 3 wherein the transparent disk is flat and the upper and lower surfaces are parallel to each other.

5. The lighting device of claim 4 wherein a portion of the reflective member opposite the annular ring light emitting luminous surface is coated white to scatter-reflect the light.

6. The lighting device of claim 5 wherein the reflective member, located other than the coated white portion, is a reflecting mirror.

7. The lighting device of claim 5 wherein the light emitting luminous surface provides a light scattering property with a frosted surface.

* * * * *